United States Patent [19]
Cleary

[11] Patent Number: 6,123,544
[45] Date of Patent: Sep. 26, 2000

[54] METHOD AND APPARATUS FOR PRECISE BOND PLACEMENT OF ORTHODONTIC APPLIANCES

[75] Inventor: James D. Cleary, Glendora, Calif.

[73] Assignee: 3M Innovative Properties Company, St. Paul, Minn.

[21] Appl. No.: 09/216,310

[22] Filed: Dec. 18, 1998

[51] Int. Cl.[7] .................................................. A61C 3/00
[52] U.S. Cl. ................................... 433/24; 433/3; 433/74
[58] Field of Search ....................... 433/24, 3, 74

[56] References Cited

U.S. PATENT DOCUMENTS

| | | | |
|---|---|---|---|
| Re. 35,169 | 3/1996 | Lemchen et al. | 433/24 |
| 3,738,005 | 6/1973 | Cohen et al. | 433/24 |
| 3,922,786 | 12/1975 | Lavin | 433/74 |
| 3,949,478 | 4/1976 | Schinhammer | 433/24 |
| 4,014,096 | 3/1977 | Dellinger | 433/24 |
| 4,155,164 | 5/1979 | White | 433/3 |
| 4,183,141 | 1/1980 | Dellinger et al. | 433/24 |
| 4,360,341 | 11/1982 | Dellinger | 433/24 |
| 4,455,137 | 6/1984 | Diamond | 433/3 |
| 4,501,554 | 2/1985 | Hickham | 433/24 |
| 4,526,540 | 7/1985 | Dellinger | 433/24 |
| 4,657,508 | 4/1987 | Dellinger | 433/24 |
| 4,812,118 | 3/1989 | Creekmore | 433/2 |
| 4,850,864 | 7/1989 | Diamond | 433/3 |
| 5,011,405 | 4/1991 | Lemchen | 433/24 |
| 5,035,612 | 7/1991 | Martin et al. | 433/3 |
| 5,055,038 | 10/1991 | Ronay et al. | 433/24 |
| 5,064,368 | 11/1991 | Lavin | 433/2 |
| 5,139,419 | 8/1992 | Andreiko et al. | 433/24 |
| 5,338,198 | 8/1994 | Wu et al. | 433/213 |
| 5,368,478 | 11/1994 | Andreiko et al. | 433/24 |
| 5,683,243 | 11/1997 | Andreiko et al. | 433/3 |
| 5,791,896 | 8/1998 | Ipenburg | 433/3 |
| 5,863,198 | 1/1999 | Doyle | 433/3 |
| 5,879,158 | 3/1999 | Doyle et al. | 433/24 |

FOREIGN PATENT DOCUMENTS

| | | |
|---|---|---|
| 349522 | 3/1990 | European Pat. Off. . |
| WO 97/03622 | 2/1997 | WIPO . |
| WO99/16380 | 4/1999 | WIPO . |

OTHER PUBLICATIONS

Rekow, Dianne, "Computer–Aided Design and Manufacturing in Dentistry: A Review of the State of the Art", *The Journal of Prosthetic Dentistry*, Oct., 1987, vol. 58, No. 4, pp. 512–516.

*Primary Examiner*—John J. Wilson
*Attorney, Agent, or Firm*—James D. Christoff

[57] ABSTRACT

A method and apparatus is provided for precisely positioning and bonding orthodontic appliances such as brackets and buccal tubes to a patient's teeth. The method and apparatus includes the use of a transfer tray and arms that are connected to the transfer tray. Orthodontic appliances are releasably connected to the arms and detached from the arms once the adhesive used for bonding the appliances to the tooth surfaces has sufficiently hardened. In certain embodiments, the transfer tray has a shape that helps hold the tray immobile relative to the patient's teeth also facilitates cleanup of any adhesive extruded from the base of the appliances during bonding. In other embodiments, fixture components are connected to the tray and include analogs for each orthodontic appliance. In certain embodiments, the tray is made by placing matrix material over arms for supporting orthodontic appliances or appliance analogs.

61 Claims, 4 Drawing Sheets

METHOD AND APPARATUS FOR PRECISE BOND PLACEMENT OF ORTHODONTIC APPLIANCES

BACKGROUND OF THE INVENTION

1. Field of the Invention

This invention relates to a method and apparatus for bonding orthodontic appliances such as brackets to a patient's teeth. More specifically, the present invention relates to a bonding method for orthodontic appliances wherein precise positioning of each appliance on the patient's teeth is carried out in part by use of a transfer tray and fixture components connected to the transfer tray.

2. Description of the Related Art

Orthodontic treatment involves movement of malpositioned teeth to orthodontically correct locations. During treatment, tiny appliances known as brackets are often fixed to the patient's anterior, cuspid and bicuspid teeth, and an archwire is placed in a slot of each bracket. The archwire forms a track to guide movement of the teeth to desired locations. Ends of the archwire are often connected to buccal tubes that are in turn secured to the patient's molar teeth. The brackets, buccal tubes and archwires are commonly referred to as "braces".

One type of orthodontic treatment technique is called the "level-arch" technique, and involves placing the brackets on the patient's teeth at certain selected locations so that the "U"-shaped archwire extends in a generally level plane at the conclusion of treatment. When the archwire is initially installed on the brackets, the malpositioned teeth may cause the wire to deviate from its normally planar configuration (in horizontal view) and from its normally smoothly curved configuration (in plan view). However, the inherent resiliency of the archwire tends to urge the brackets and hence the associated teeth toward a level array wherein the archwire re-assumes its normally planar and smoothly curved configuration. The level-arch technique is considered satisfactory by many orthodontists because the need for bends, steps or other adjustments in the archwire is reduced and in many cases eliminated, resulting in a savings of time for both the orthodontist as well as the patient.

As can be appreciated, the degree of success of the level-arch technique is related in part to the position and orientation of the brackets and buccal tubes on the patient's teeth. For example, if one of the brackets is bonded to a patient's tooth at a location that is too close to the patient's gingiva (i.e., the patient's gums) relative to the placement of brackets on adjoining teeth, that tooth will protrude outwardly an excessive distance in an occlusal direction (i.e., in a direction toward the outer tips of the patient's teeth) relative to adjoining teeth at the conclusion of treatment if all of the brackets are aligned in a level array. In such an instance, the orthodontist can correct the orientation of the malpositioned tooth by placing bends or steps in the archwire at locations adjacent each side of its bracket, but such a practice entails additional work for the orthodontist and may also increase the overall length of treatment time.

As a consequence, many suggestions have been made in the past for improving the placement accuracy of orthodontic appliances during the procedure of bonding the appliances to the patient's teeth. For example, height gauges such as the well-known "Boone" gauge provide a means for indicating a desired position of the appliance on a tooth relative to the occlusal edge of the associated tooth. The Boone gauge has a flat surface that is placed over the occlusal edge of the tooth, and a fixed pin spaced from the flat surface scribes a mark to indicate the desired occlusal-gingival position of the archwire slot of the appliance on the tooth. Once the mark has been scribed, a small quantity of adhesive is placed or "buttered" on the base of the appliance and a tweezers or other hand instrument is used to place the appliance on the chosen tooth. Next, the appliance is shifted as may be necessary to bring the appliance to the selected position.

A somewhat similar device is known as a positioning jig, and is supplied by the manufacturer of the appliance as a component to be disposed of once the appliance has been properly positioned on the selected tooth. An example of a positioning jig for use with an orthodontic bracket is described in U.S. Pat. No. 5,429,229, and is made of a flexible plastic material having stirrups that are received over occlusal and gingival edges of tiewings of the bracket. The jig described in U.S. Pat. No. 5,429,229 can be grasped by a suitable hand instrument and used to support the bracket during placement and bonding of the bracket to the tooth. The jig includes stepped portions that are intended for alignment with the occlusal edge of the selected tooth. Once the adhesive has hardened and the bracket is securely bonded to the tooth, the positioning jig is released from the bracket by bending the jig until the stirrups disengage the tiewings.

Other types of appliance positioning devices are described, for example, in U.S. Pat. Nos. 4,455,137 and 4,850,864. In the device of U.S. Pat. No. 4,850,864, the appliance is grasped by opposed jaws, and the device also includes a gauge for placing the appliance on a tooth surface at a location that is a pre-determined distance from the occlusal edge of the tooth. Another example of a positioning device is known as the "Dougherty" gauge, which has a blade that is received in the archwire slot of the appliance to support the appliance during bonding. The Dougherty gauge also has an arm that is spaced a fixed distance from the blade, and the arm is placed in contact with the occlusal edge of the tooth during bonding so that as a consequence the appliance is positioned a pre-determined distance from the tooth's occlusal edge.

While the bonding techniques described above are considered satisfactory by some practitioners, there are shortcomings that are inherent with such techniques. For example, access to the surfaces of certain malpositioned teeth (such as the bicuspid and molar teeth) may be difficult. In some instances, and particularly in connection with posterior teeth, the practitioner may have difficulty seeing the precise position of the bracket relative to the tooth surface. Another problem with the above described techniques concerns the significant length of time needed to carry out the procedure of positioning and bonding a bracket to each individual tooth, which is a nuisance both to the patient as well as to the orthodontist. The risk of moisture contamination from the patient's saliva also increases as the time increases that the patient is awaiting completion of the bonding procedure. The above factors may also unduly impair the accuracy of placement of the brackets on the teeth and/or increase the chance that the ultimate adhesive bond will not have sufficient strength to retain the brackets on the teeth during the course of orthodontic treatment.

Bonding techniques known as "indirect bonding" avoid many of the problems noted above. In general, indirect bonding techniques involve the use of a transfer tray having a shape that matches the configuration of at least part of one of the patient's dental arches. A set of brackets is releasably connected to the tray at certain, pre-determined locations. Once adhesive is applied to the base of each bracket, the tray is placed over the patient's teeth until such time as the adhesive hardens. Next, the tray is detached from the teeth as well as from the brackets, often with the result that all of the brackets that were previously connected to the tray are now bonded to their respective teeth at certain intended, pre-determined locations. The procedure is often duplicated for the patient's other dental arch.

In more detail, one known method of indirect bonding includes the steps of taking an impression of the patient's dental arch and then making a replica plaster or "stone" model from the impression. A sealing solution (such as Liquid Foil brand sealing solution from 3M) is applied to the stone model and allowed to dry. If desired, the teeth of the model are marked with a pencil to assist in placing the brackets in ideal positions.

Next, the brackets are temporarily bonded to the sealed stone model. Optionally, the bonding adhesive can be a chemical curing adhesive (such as Concise brand from 3M) or a light curable adhesive (such as Transbond XT or Transbond LR adhesive from 3M). Optionally, the brackets may be adhesive pre-coated brackets such as described in U.S. Pat. Nos. 5,015,180, 5,172,809, 5,354,199 or 5,429, 299.

A transfer tray is then made by placing matrix material over the model as well as over the brackets on the model. For example, a plastic sheet matrix material may be placed over the model and brackets and then heated in an oven. A vacuum source is used to evacuate air between the matrix material and the model. As the matrix material is heated, the plastic sheet material is drawn down over the model and assumes a configuration that precisely matches the shape of the replica teeth of the stone model and adjacent brackets.

The plastic model is then allowed to cool and harden to form a tray. Next, the tray and the brackets (which are embedded in an interior wall of the tray) are detached from the stone model and sides of the tray are trimmed as may be desired. The tray also may be cut into smaller sections for ease of placement during bonding. If the cured adhesive remains on the bracket base after detaching the brackets from the model, the adhesive can serve as a custom-made bonding surface having a contour that matches the contour of the patient's tooth for a snug, mating fit.

Once the patient has returned to the office, a quantity of adhesive is placed on the base of each bracket (or on the cured adhesive, if any) and the tray (or tray section) with the embedded brackets is then placed over matching portions of the patient's dental arch. Since the configuration of the interior channel in the tray closely matches the respective portions of the patient's dental arch, each bracket is ultimately positioned on the patient's teeth at precisely the same location that corresponds to the previous location of the same bracket on the stone model.

Both light-curable adhesives and chemical curing adhesives have been used in indirect bonding techniques to secure the appliances to the patient's teeth. If a light-curable adhesive is used, the tray is preferably transparent or translucent. If a two-component chemical curing adhesive is used, the components can be mixed before application to the brackets, or alternatively one component may be placed on each bracket base (or on the cured adhesive, if any) and the other component may be placed on the tooth surface. In either case, placement of the tray with the embedded brackets on corresponding portions of the patient's dental arches enables the brackets to be bonded to the teeth as a group a relatively short amount of time. With such a technique, individual placement and positioning of each bracket in seriatim fashion on the teeth is avoided.

While it is apparent that the use of certain bonding techniques such as indirect bonding can greatly facilitate placement of appliances on the patient's teeth and shorten the amount of time that the patient is occupying the chair in the operatory, there is a continuing need in the art to improve current bonding techniques in order to increase placement accuracy, optimize the use of the practitioner's time and also improve the strength of the bond between the appliance and the tooth. Moreover, there is a need in the art to reduce the time and expenses associated with making the transfer tray, so that the expense to the practitioner as well as to the patient can be correspondingly decreased.

SUMMARY OF THE INVENTION

The present invention is directed in one aspect toward a method of bonding an orthodontic appliance to a tooth. The method comprises the steps of creating a replica of a patient's tooth structure, and releasably connecting at least one fixture component to the replica, wherein each fixture component includes an orthodontic appliance analog and an arm connected to the appliance analog, and wherein each appliance analog is positioned on the replica at a location corresponding to a location on the patient's tooth structure where an orthodontic appliance is to be received. The method also includes the steps of making a transfer tray by placing matrix material over at least a portion of the replica, and detaching the transfer tray from the replica. The method further includes the steps of replacing each appliance analog with an orthodontic appliance, and applying an orthodontic adhesive on at least one of the patient's tooth structure and each orthodontic appliance. The method also includes the steps of placing the transfer tray over the tooth surface, and moving each arm relative to the transfer tray in order to bring each orthodontic appliance into contact with the patient's tooth structure.

Another aspect of the present invention is also related to a method of bonding an orthodontic appliance to a tooth. In this aspect, the method includes the steps of creating a replica of a patient's tooth structure, and releasably connecting at least one fixture component to the replica, wherein each fixture component is positioned on the replica at a location corresponding to the location on the patient's tooth structure where an orthodontic appliance is to be received. The method also includes the steps of making a transfer tray by placing matrix material over at least a portion of the replica as well as over at least a portion of at least one fixture component, and detaching the transfer tray from the replica. The method further includes the steps of disconnecting at least a portion of at least one fixture component from the transfer tray, and connecting at least one orthodontic appliance to the transfer tray at respective location(s) corresponding to the previous location(s) of at least one of the disconnected fixture components or component portions. The method also includes the steps of applying an orthodontic adhesive on at least one of the patient's tooth structure and each orthodontic appliance to be bonded, and placing the transfer tray with each orthodontic appliance over the patient's corresponding tooth structure in order to bond each orthodontic appliance to the tooth structure.

Another aspect of the present invention is directed toward a method of bonding an orthodontic appliance to a tooth that comprises the steps of making a transfer tray that corresponds to a negative image of at least part of the patient's tooth structure, and connecting at least one carrier arm to the tray in such a manner that at least one carrier arm is movable relative to the tray. The method also includes the steps of releasably coupling an orthodontic appliance to at least one carrier arm, and placing the tray over the patient's tooth structure. The method further includes the steps of applying an orthodontic adhesive on at least one of the patient's tooth structure and each appliance, and moving at least one carrier arm relative to the tray in order to bond the appliance coupled to such arm(s) to the patient's tooth structure. The step of making the transfer tray includes the step of making portions that extend along mesial and distal sides of at least one appliance at a position spaced from the appliance in order to facilitate removal of any excess adhesive.

In yet another aspect, the present invention is directed toward an orthodontic transfer tray assembly for indirect bonding. The assembly includes at least one orthodontic appliance and at least one carrier arm, wherein each carrier arm is connected to a corresponding orthodontic appliance. The assembly also includes a transfer tray having an occlusal section for extending over occlusal portions of the patient's tooth structure and a buccolabial section for extending over buccolabial portions of the patient's tooth structure. Each carrier arm is coupled to the tray. The buccolabial section includes a generally "U"-shaped recess for receiving each appliance. Each recess extends along the mesial, occlusal and distal sides of the corresponding appliance in spaced relationship from the appliance when the appliance is in contact with the patient's tooth structure.

The present invention is also directed toward an orthodontic transfer tray that comprises at least one orthodontic appliance and at least one carrier arm, wherein each carrier arm is connected to a corresponding appliance. The assembly includes a transfer tray having a generally "U"-shaped channel for extending along the patient's dental arch. The tray includes a lingual section, a buccolabial section and an occlusal section interconnecting the lingual section and the buccolabial section. The lingual section and the buccolabial section are resilient and have sufficient depth in a generally occlusal-gingival direction to present undercut regions that snap-fit over corresponding tooth structure for self-retaining the tray in engagement with the tooth structure in releasable fashion. The tray also includes at least one passageway extending in the occlusal section for receiving a respective carrier arm.

The present invention is additionally directed toward a method of making a transfer tray assembly for an orthodontic patient. The method comprises the steps of supporting at least two orthodontic appliances or appliance analogs at selected, spaced-apart positions, and coupling a corresponding arm to each orthodontic appliance or appliance analog. A quantity of matrix material is placed over at least a portion of each arm in order to connect the arms together. At least a portion of the matrix material has a configuration matching at least a portion of the orthodontic patient's dental arches. The matrix material is allowed to harden to form a tray.

Another embodiment of the invention is also directed toward a method of making a transfer tray for an orthodontic patient. The method according to this embodiment includes the steps of creating a replica of the patient's tooth structure, and releasably connecting at least one fixture component to the replica. Each fixture component includes an orthodontic appliance analog and an arm connected to the appliance analog. Each appliance analog is positioned on the replica at a location corresponding to a location on the patient's tooth structure where an orthodontic appliance is to be received. Matrix material is placed over at least a portion of the replica as well as over at least a portion of the arm of at least one fixture component. The transfer tray is detached from the replica, and each appliance analog is replaced with an orthodontic appliance.

The methods and apparatus of the present invention are advantageous for a number of reasons. The use of appliance analogs according to some embodiments of the invention is an advantage, in that the appliance analogs can be re-used a number of times for making different transfer trays and the appliances that are ultimately bonded to the patient's teeth need not be obtained or used until the transfer tray has been made. As a result, the risk of contamination or other injury to the appliance is reduced. Other aspects of the invention that are directed toward a transfer tray having portions extending along mesial and distal sides of the appliance in spaced relationship to the appliance are an advantage, in that excess adhesive can be expressed from the base of the appliance during the bonding procedure without hindrance from the tray and can be readily removed using an explorer or other dental tool before the adhesive has hardened. Other aspects of the invention that include the step of making a transfer tray by placing matrix material over at least a portion of each fixture component are advantageous because each fixture component is properly orientated with respect to the transfer tray without the need for manual adjustments or the like.

These and other features of the invention along with their advantages are described in the text that follows and are illustrated in the accompanying drawings.

DETAILED DESCRIPTION OF THE PREFERRED EMBODIMENTS

The following description sets out in detail a method and apparatus for bonding orthodontic appliances to teeth according to presently preferred embodiments of the invention. The method and apparatus set out below represent examples of the invention for illustrative purposes only and should not be construed as a limitation to the invention, since those skilled in the art may recognize that a number of modifications and additions may alternatively be employed.

Figure 1:
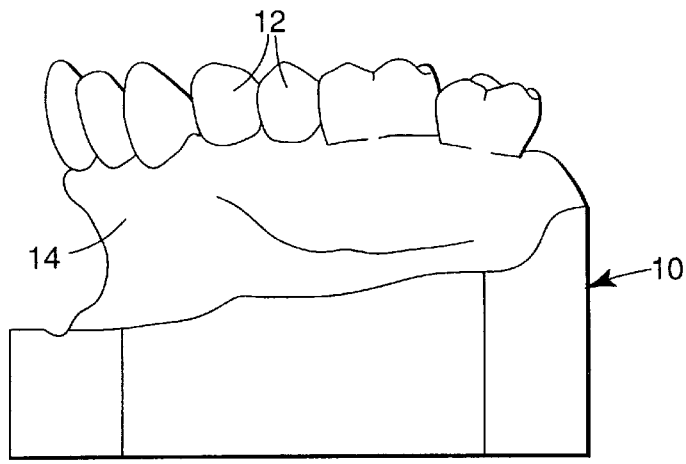
FIG. 1 is a side elevational view of an exemplary replica of a patient's upper dental arch, as is useful in partially carrying out a method of bonding orthodontic brackets according to one aspect of the present invention.

FIG. 1 is an illustration of an example of a model or replica arch 10 of a patient's upper dental arch. The replica arch 10 includes a number of replica teeth 12 as well as adjacent portions of replica soft tissue 14 that are similar in shape to the patient's soft tissue or "gums". Preferably, although not necessarily, the replica arch 10 includes replicas of all of the teeth in the patient's upper (or lower) arch. If the impression is accurately taken and the replica dental arch 10 is carefully prepared, the replica teeth 12 and replica soft tissue 14 will have a configuration and orientation that are identical to the configuration and orientation of the corresponding teeth and soft tissue of the orthodontic patient.

The replica arch 10 can be prepared by any one of a number of suitable known methods. For example, the replica arch 10 may be prepared by first taking an impression of the patient's upper dental arch, taking care to avoid undue distortion. Preferably, an alginate impression material is used such as Unijel-II brand alginate impression material from 3M Unitek. Alternatively, a hydrocolloid or a vinyl polysiloxane impression material may be used, such as Imprint brand vinyl polysiloxane impression from 3M. Next, the replica arch 10 is made from each impression using, for example, a material such as plaster of Paris. Preferably, the replica arch is substantially free of voids. If voids are present, the voids can be filled with a small, additional quantity of suitable material such as plaster of Paris.

As an alternative, the replica arch 10 may be prepared by generating digital information defining the shape of the patient's upper dental arch, and then using the digital information to create a replica. For example, the digital information may be created by the methods set out in PCT application no. WO 97/03622 which is expressly incorporated by reference herein. In brief, PCT application no. WO 97/03622 describes a method of generating digital information of a patient's dental arches by making an impression of the patient's arches, and then removing a layer from the impression (or alternatively removing a layer from a model made from the impression) to obtain a flat surface; a video camera or other device is then used to collect digital data of the flat surface and the method is repeated; finally, the data is combined to provide a data set representative of the configuration of the patient's dental arches.

Other means for generating digital information of the patient's dental arch may also be employed. For example, the digital information may be generated electromechanically (e.g., stylus scanning), by laser scanning, by photogammetry, by sonic ranging, by digital video scanning or magnetically. Examples of devices for generating the information are described in an article by Rekow entitled "*Computer Aided Design and Manufacture in Dentistry: A Review of the State of the Art*", from the Journal of Prosthetic Dentistry, Vol. 58, page 512 (1987) which is expressly incorporated by reference herein. Other examples are described in U.S. Pat. Nos. 5,078,599, 5,131,844, 5,338,198, 4,611,288 and 5,372,502 as well as in an article entitled "*Three-dimensional dental cast analyzing system with laser scanning*" (Kuroda, et al., Am. J. Ortho. Dent. Othrop., Vol. 110 [4], October 1996, pages 365–69).

Once the replica arch 10 has been prepared, a layer of separating medium is applied to the replica arch 10 if desired. For example, if the replica arch 10 is made of plaster of Paris, a thin layer of separating medium such as Liquid Foil brand sealing solution from 3M or Al-Cote brand separating medium from Dentsply is applied to the replica arch 10 and allowed to dry.

Next, a determination is made as to the preferred intended position of each orthodontic appliance when ultimately bonded to the corresponding teeth of the patient and that position is indicated on the replica teeth. As one example, a pencil mark may be made across the labial surface of each replica tooth 12 with the assistance of a height gauge such as a Boone bracket positioning gauge from 3M Unitek (Catalog No. 807-002). The pencil line is drawn across the labial surface of each replica tooth 12 in a mesial-distal direction, preferably as a locator guide for ultimate placement of the archwire slot of each orthodontic appliance on the patient's teeth. Optionally, a pencil line may also be drawn across the labial surface of each replica tooth 12 in a generally occlusal-gingival direction to mark the central long axis of the tooth 12.

The distance of the mesial-distal pencil line from the occlusal edge of the replica tooth 12 may vary in accordance with the treatment technique employed by the practitioner and the type of orthodontic appliance to be used by the practitioner. The distance of the pencil line from the occlusal edge of the replica teeth 12 may also vary in accordance with the type of tooth. For example, the distance of the pencil mark from the occlusal edge of replica anterior teeth may be less than the distance of the pencil mark from the occlusal edge of replica cuspid and bicuspid teeth. Other types of gauges may also be used, such as the Dougherty bracket positioning gauge from 3M Unitek.

Figure 2:
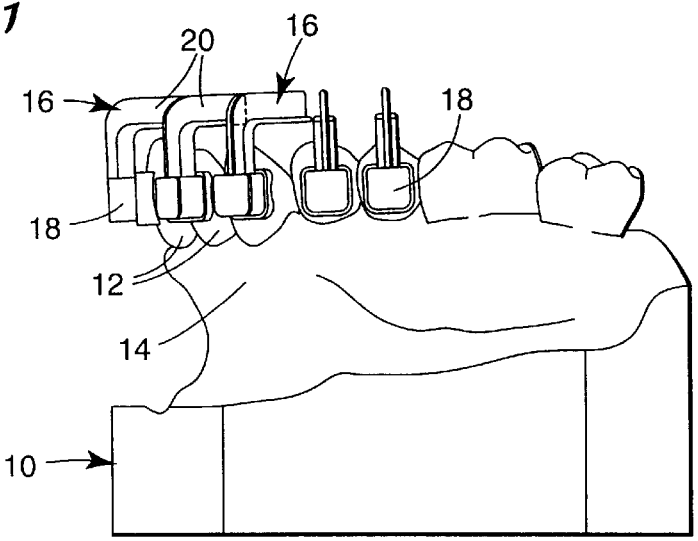
FIG. 2 is a view somewhat similar to FIG. 1 except that fixture components have been connected to some of the teeth of the replica for purposes of illustration.

Next, a fixture component 16 is temporarily secured to each replica tooth 12 that is to be bonded using a transfer tray. In FIG. 2, a fixture component 16 has been secured to each replica tooth 12 except for replica molar teeth. Each fixture component 16 includes an orthodontic appliance analog 18 and a fixture arm 20 that is connected to each appliance analog 18. An adhesive such as 3M Unitek Laboratory Adhesive for Indirect Bonding (catalog no. 704-050) can be used to temporarily bond the appliance analog 18 to the replica tooth 12. Alternatively, a mechanical coupling or a holding fixture can be provided to releasably connect each appliance analog 18 to the corresponding replica tooth 12 during the subsequent steps of making the tray as described below.

Each fixture arm 20 has a generally L-shaped configuration in side view, with a first portion that extends in an occlusal direction from the associated appliance analog 18 and a second portion that extends in a lingual direction from the occlusal end of the first portion. Both the first portion and the second portion of the fixture arm 20 are preferably spaced from the buccolabial and occlusal sides respectively of the associated replica tooth 12 when the fixture component 16 is secured to the replica tooth 12.

The fixture arm 20 preferably has a non-circular cross-sectional shape. In the embodiment shown in the drawings, the fixture arm has a generally "T"-shaped configuration. Other cross-sectional configurations may also be employed, such as rectangular, "X"-shaped, "L"-shaped and the like. Preferably, the appliance analog 18 has a base facing the associated replica tooth 12 that is larger in a mesial-distal direction (i.e., in a direction extending along the length of the dental arch) than the overall mesial-distal dimension of the base of the orthodontic appliance that is ultimately to be received on the corresponding tooth of the patient.

Additionally, the appliance analog 18 has a base that preferably is larger in an occlusal-gingival direction than the overall occlusal-gingival dimension of the same appliance. Preferably, the fixture components 16 are made of a material suitable for numerous re-uses, such as hard tool steel or the like.

Optionally, the appliance analogs 18 have scribe marks, paint markings, indicia or other features to facilitate aligning the appliance analogs 18 with the mesial-distal and occlusal-gingival pencil marks previously made on the labial surface of each corresponding replica tooth 12. If, for example, the fixture components 16 are placed on the replica teeth 12 by hand, the fixture components 16 can be shifted slightly as needed after initial placement on the replica teeth 12 in order to bring such scribe marks or other indicia into precise alignment with the pencil marks on the replica teeth 12. An another option, the fixture components 16 may include tabs or gauges intended for contact or visual alignment with the occlusal edge of replica teeth 12 and oriented such that the appliance analog 18 is properly positioned on the replica tooth 12 in an occlusal-gingival direction when the tab is brought into contact or alignment with the occlusal edge of the same replica tooth.

As an alternative, other types of placement devices may be used to position the analogs 18 on the replica teeth 12. For example, hand-held devices that releasably grasp the analogs 18 can be employed, such as the devices described in U.S. Pat. Nos. 4,455,137 and 4,850,864. Preferably, those devices include gauges or jigs to position the analogs 18 on the replica teeth 12 at precise locations. As another example, bond placement devices useful in indirect bonding procedures such as the devices described in U.S. Pat. No. 4,812,118 may be used.

Figure 2A:
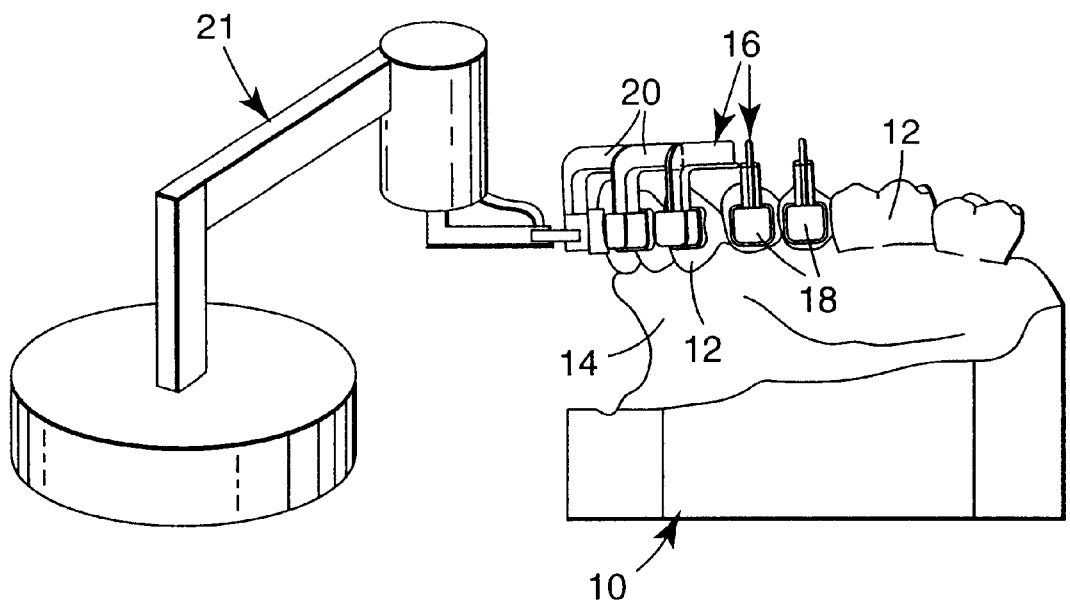
FIG. 2a is a view somewhat similar to FIG. 2 except that a robotic arm is used to place the fixture components on the replica teeth.

As another alternative, an automated device such as a computer controlled robotic arm 21 as shown in FIG. 2a may be used for precise placement of each fixture component 16 on the associated replica tooth 12. In that instance, software can be used to determine placement of the appliance analogs 18 and the use of pencil marks on the replica teeth 12 for alignment of the appliance analogs 18 may be omitted. For example, if the replica dental arch 10 is made using digital information, a computer may be used to calculate an idealized position for each orthodontic appliance on the patient's teeth, and that information can then be used in a set of instructions to control movement of the robotic arm 21 such that the appliance analog 18 is placed on the corresponding, selected location of the associated replica tooth 12. Optionally, a series of robotic arms may be used to releasably connect the fixture components 16 to corresponding replica teeth 12 during the steps of making a tray as described below.

Figure 3:
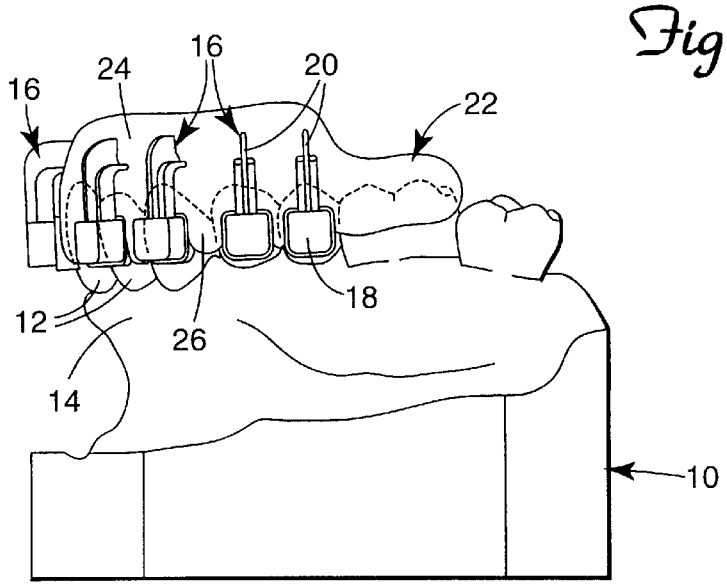
FIG. 3 is a view somewhat similar to FIG. 2 except that a quantity of matrix material has been placed over some of the replica teeth as well as over portion of arms of the fixture component in order to make a transfer tray.

After the appliance analogs 18 have been bonded or otherwise connected to the replica teeth 12, a quantity of matrix material is applied to the replica dental arch 10 and a portion of the fixture components 16. In particular, the matrix material is applied to the replica dental arch 10 and the lingually-extending second portion of the fixture arm 20, but is preferably not applied over the first portion of the arms 20 or over the appliance analogs 18. FIG. 3 is an illustration of matrix material that has been applied to the replica teeth 12 that have received a fixture component 16, as well as an adjacent replica molar tooth. The matrix material is then hardened or allowed to harden to form a transfer tray 22.

Examples of suitable matrix materials include materials that are liquid or semi-liquid and subsequently harden, as well as sheet materials that are softened and then hardened. Optionally, two layers of matrix materials may be utilized: a first layer of a liquid material that provides precise replication of the underlying surfaces, followed by a second layer of a material that has a semi-liquid or putty consistency.

Optionally, the matrix material may comprise two or more layers, where the resulting transfer tray 22 has an outer layer that is more rigid than an inner layer. The outer layer provides rigidity to the transfer tray 22, while the more flexible inner layer facilitates subsequent removal of the transfer tray 22 from the replica dental arch 10, particularly when the transfer tray 22 includes portions to be received in undercut regions of the patient's dental arch.

Preferably, the transfer tray 22 includes a generally "U"-shaped channel that extends along the length of the replica dental arch 10. The tray 22 includes a lingual section, a buccolabial section and an occlusal section interconnecting the lingual section and the buccolabial section. Preferably, both the lingual section and the buccolabial section extend in a gingival direction a distance sufficient to pass over at least some of the interproximal areas next to the replica soft tissue. Those areas often include undercut regions and protruding regions that subsequently serve to securely couple the transfer tray 22 to the patient's dental arch.

As illustrated in FIG. 3, the occlusal section 24 projects in an occlusal direction from the occlusal edge of the replica teeth 12. The second portion of the fixture arm 20 (i.e., the portion that extends in a labial-lingual direction) is embedded in the occlusal section 24, and preferably extends completely through the occlusal section 24. Preferably, the regions of the occlusal section 24 that receive the second portion of the fixture arms 20 is made of relatively rigid material.

Preferably, the buccolabial section of the transfer tray 22 includes portions 26 (FIG. 3) that extend along mesial and distal sides of the appliance analogs 18. Optionally, but not necessarily, the mesial and distal portions 26 abut the mesial and distal sides of the appliance analogs 18, and extend in a gingival direction along at least a majority of the length of the mesial and distal sides of the appliance analogs 18. Moreover, at least some of the mesial and distal portions 26 may optionally extend beyond the gingival side of adjacent appliance analogs 18 in a gingival direction.

Next, the transfer tray 22 as well as the fixture components 16 are removed from the replica dental arch 10. Optionally, the fixture components 16 are detached from the transfer tray 22 before the transfer tray 22 is separated from the replica arch 10. The fixture components 16 are released if desired from the transfer tray 22 by sliding the second portion of the fixture arms 20 in a buccolabial direction until the arms 20 are removed from the passageways that were formed by embedding the arms 20 in the matrix material. Optionally, the fixture arms 20 may be made of or coated with a low-friction, lubricous and/or release material such as fluoropolymers in order to facilitate sliding movement of the fixture components 16 in the passageways. An example of a suitable lubricating material that is available as an aerosol and may be sprayed onto the fixture arms 20 is MS-122 Fluorocarbon Release Agent Dry Lubricant from Miller-Stephenson.

Next, the transfer tray 22 is trimmed as needed to remove excess material. Optionally, the transfer tray 22 is cut into two sections corresponding to each quadrant of the patient's upper dental arch in order to facilitate the subsequent steps as described below. As other alternatives, the transfer tray 22 may be cut into a greater number of sections, such that each resulting section corresponds to less than a quadrant of the patient's upper dental arch. The transfer tray 22 may optionally be cut into small sections that correspond to only a single tooth if so desired.

Figure 5:
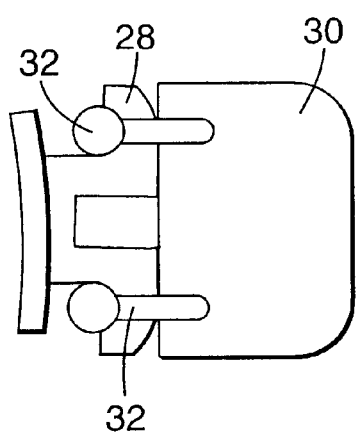
FIG. 5 is an enlarged side elevational view of one of the orthodontic appliances and part of an associated carrier arm as shown in FIG. 4.
Figure 6:
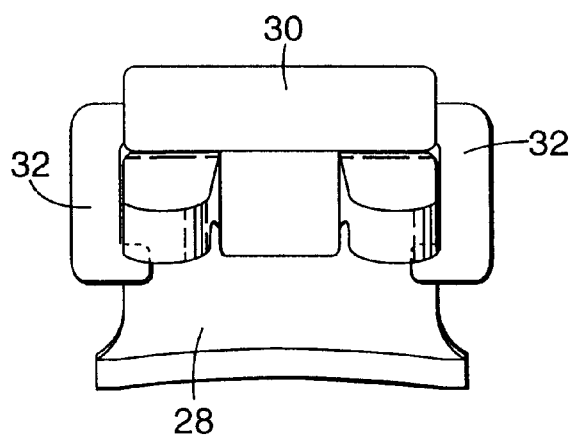
FIG. 6 is an enlarged plan view of the appliance and carrier arm shown in FIG. 5 looking toward a occlusal side of the appliance.
Figure 4:
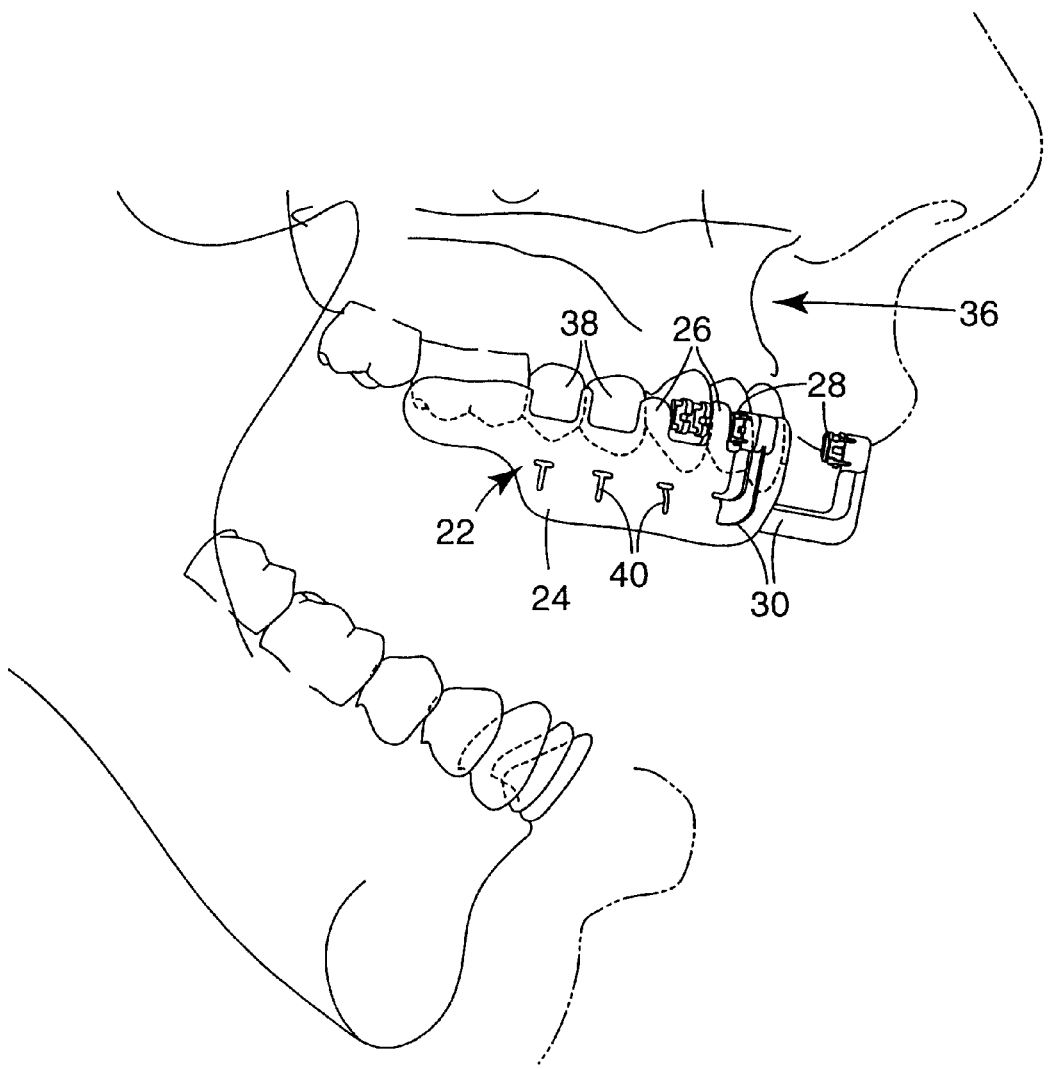
FIG. 4 is a side elevational view in partially schematic form of upper and lower dental arches of a patient, wherein the transfer tray illustrated in FIG. 3 has been placed over tooth structure of the patient's upper dental arch, except that the fixture components illustrated in FIG. 3 have been removed and replaced in some instances with exemplary orthodontic brackets and carrier arms connected to the brackets.

Next, each fixture component 16 is replaced with an orthodontic appliance 28 and a carrier or carrier arm 30, two examples of which are shown in FIG. 4. The fixture components 16 may be replaced with the appliances 28 in a manual procedure or in an automated procedure using robotic arms or the like. In the illustrated embodiments the carrier arm 30 is releasably connected to the appliance 28 by a pair of flexible stirrups 32 that are shown in more detail in FIGS. 5 and 6. The stirrups 32 snap into notches behind occlusal and gingival tiewings of the appliance 28 in order to releasably connect the appliance 28 to the carrier arm 30.

Optionally, the carrier arm 30 also includes a slot segment (not shown) that is received in an archwire slot of the appliance 28 when the appliance 28 is connected to the carrier arm 30. The slot segment serves to stabilize the appliance 28 and hinder undue movement of the latter relative to the carrier arm 30. Optionally, the slot segment has an interference fit with the archwire slot, or has movable portions that expand to tightly fit within the archwire slot so that the stirrups 32 may be omitted.

Other coupling structure may alternatively be employed to releasably connect the carrier arm 30 to the orthodontic appliance 28. For example, the carrier arm 30 may be provided with flexible stirrups of the type described in U.S. Pat. No. 5,429,229. Alternatively, the carrier arm 30 may have movable jaws that releasably clamp against the mesial and distal sides of the appliance 28. As another alternative, a substance having a gummy consistency and/or exhibiting adhesive characteristics may be utilized as a temporary coupling. As a further option, the carrier arm 30 and the orthodontic appliance 28 may be initially integrally joined together by a frangible web that is fractured (e.g., by bending or cutting) after the appliance 28 is bonded to the patient's tooth.

The transfer tray 22 is then placed over the patient's tooth structure that corresponds to the replica teeth 12. In the example shown in FIG. 4, the transfer tray 22 has been placed over the patient's upper dental arch 36, including teeth 38.

Before the transfer tray 22 is placed over the dental arch 36, the carrier arms 30 are retracted sufficiently in the passageways 40 to ensure that any adhesive on the base of the appliance 28 is located buccolabially of the buccolabial side of the tray channel. As a result, the adhesive will not smear or otherwise contact the patient's tooth surface during placement of the transfer tray 22, a distinct advantage in contrast to many conventional indirect bonding methods. Once the transfer tray 22 is in place the undisturbed adhesive on the base of the appliances 28 can be brought into contact with the patient's teeth at any convenient time upon movement of the carrier arms 30 in a lingual direction.

Preferably, the transfer tray 22 is releasably received on the patient's upper dental arch 36 in secure fashion such that the transfer tray 22 is relatively immobile relative to the patient's teeth 38. To this end, the undercut regions and protruding regions of the transfer tray 22 as described above facilitate the immobilization of the transfer tray 22 on the upper dental arch 36. Additionally, the mesial and distal portions 26 of the transfer tray 22 engage underlying tooth structure adjacent the appliances 28 to further help immobilize the transfer tray 22.

A suitable orthodontic bonding adhesive is applied to the base of each orthodontic appliance 28. Examples of suitable bonding adhesives include light-curable adhesives such as Transbond XT or Transbond LR adhesives from 3M Unitek. As another option, two-component chemical curing adhesives that begin to cure when mixed together may also be used, such as Concise brand adhesive from 3M. If a two-component adhesive is used, the components may be mixed together and then applied to the appliances 28. Alternatively, if the appliance base closely matches the configuration of the tooth surface, one component of a two-component adhesive may be applied to the tooth surface and the other component applied to the appliance 28, such that the components are mixed when the appliance 28 is pressed against the tooth 38. An example of a suitable two-component adhesive is described in pending U.S. patent application Ser. No. 09/126,069, now U.S. Pat. No. 5,971,754 entitled "Indirect Bonding Method and Adhesive for Orthodontic Treatment", which is co-owned with the present application and expressly incorporated by reference herein. The adhesive or adhesive components may be applied to the appliance and/or the tooth surface by any suitable method, such as by a "buttering" technique, by brushing or by wiping.

FIG. 4 also shows passageways 40 that extend through the occlusal section 24 of the transfer tray 22. The passageways 40 were formed by the second portions of the fixture arms 20 once embedded in the matrix material as described above, and remain in the occlusal section 24 after separation of the fixture arms 20 from the transfer tray 22. Preferably, the carrier arms 30 have a lingually extending occlusal portion that has a cross sectional configuration identical to the cross-sectional configuration of the second portion of the corresponding fixture arm 20, so that the carrier arm 30 is slidable in a longitudinal direction in the passageway 40 but is substantially prevented from movement in a lateral direction (i.e., movement in a mesial-distal direction or an occlusal-gingival direction).

Preferably, the carrier arms 30 and the associated appliances 20 are connected to the transfer tray 22 before the transfer tray 22 is placed over the patient's upper dental arch 36. As an alternative, however, the transfer tray 22 may be first placed on the patient's dental arch 36 and subsequently each of the carrier arms 30 along with the associated appliance 28 is connected to the tray 22 by inserting the carrier arms 30 into the respective passageways 40.

Next, the appliances 28 are bonded to the buccolabial surfaces of the patient's teeth 38 by sliding the carrier arms 30 in a lingual direction, preferably using finger pressure. Advantageously, the use of finger pressure provides tactile feedback, so that the practitioner can determine when the appliance 28 has been seated with sufficient force against the surface of the patient's tooth 38 to create a satisfactory bond. The tactile feedback also helps the practitioner confirm that the adhesive has a proper viscosity and is present in sufficient quantity. Alternatively, however, a mechanical or pneumatic device may be employed (such as a piston and cylinder assembly or solenoid assembly) to move the arms 30 in lingual (and also optionally in labial) directions.

Preferably, enough bonding adhesive is provided so that a small quantity of adhesive is extruded from all four sides of the appliance 28 as the appliance is pressed against the tooth surface. In this manner, the likelihood of the presence of any small voids or recesses in the adhesive is substantially reduced. It is preferred to avoid recesses and voids in the adhesive, since such recesses and voids might otherwise reduce the strength of the bond between the appliance 28 and the associated tooth 38. Recesses and voids may also provide a location that can collect food or other debris that can result in the formation of caries.

As mentioned above, the base of the orthodontic appliance 28 preferably has overall mesial-distal and occlusal-gingival dimensions that are less than the corresponding mesial-distal and occlusal-gingival overall dimensions of the appliance analog 18. As a consequence, the transfer tray 22 including the mesial and distal portions 26 are spaced from adjacent sides of the appliance 28 when the appliance 28 is pushed against the outer surface of the tooth 38 for bonding. The spacing between the appliance 28 and the transfer tray 22 provides an open recess area where adhesive can be freely expressed from the base of the appliance 28 as the latter is urged toward the tooth 38, and allows the practitioner to visually confirm that sufficient adhesive is present to provide at least some extrusion of adhesive from at least one side of the appliance 28.

Additionally, the space between the appliance 28 and adjacent portions of the tray 22 facilitates clean-up of adhesive extruded from the area between base of the appliance 28 and the tooth 38. The space conveniently allows a dental explorer or other tool to be moved along all sides of the appliance 28 in order to remove excess adhesive from the tooth surface adjacent edges of the appliance 28.

The use of a light-curable adhesive to bond the appliance 28 to the tooth 38 is an advantage since the excess adhesive can be removed at the practitioner's convenience without undue premature hardening of the adhesive. Optionally, the transfer tray 22 is transparent or translucent to actinic radiation in order to facilitate directing the light toward the adhesive. The above-mentioned space between the appliance 28 and the transfer tray 22 also helps the light reach the adhesive.

Optionally, the appliances 28 have a base that has a coating of light-curable adhesive applied by the manufacturer. Such adhesive pre-coated appliances are described, for example, in U.S. Pat. Nos. 5,015,180, 5,172,809, 5,354,199 and 5,429,299, all of which are assigned to the assignee of the present invention and incorporated by reference herein.

The appliances 28 may be any bondable orthodontic device such as brackets, buccal tubes and the like. The appliances 28 may be made of any suitable material such as metal (e.g., stainless steel), ceramic (e.g., translucent polycrystalline alumina or transparent single crystal alumina) or plastic (e.g., translucent polycarbonate). Examples of suitable appliances 28 include essentially all commercially available direct-bond brackets and buccal tubes as well as various appliances known in the literature including the patent literature.

As an option, the transfer tray 22 is made in a dental laboratory or by an orthodontic appliance manufacturer after receiving an impression or an electronic data file representative of the patient's dental arches. Consequently, the dental laboratory or the manufacturer can re-use the fixture components 16 a number of times. Once the transfer tray 22 has been made, the appliances 28, carrier arms 30 and transfer tray 22 (or tray sections) are assembled and preferably shipped to the orthodontist as single units, ready for use with minimal further preparation at the orthodontist's office.

Preferably, the carrier arms 30 are made of a relatively inexpensive material such as plastic that can be disposed of after a single use. Optionally, the fixture arms 20 also serve as the carrier arms 30. In that instance, the fixture arm 20 are releasably connected to the appliance analog 18, so that the arms 20 can be subsequently releasably coupled to an appliance such as the appliances 28. The releasably couplings as described above in various forms in connection with the carrier arms 30 may be used to detachably connected the appliance analogs 18 to the fixture arms 20.

As another option, each fixture arm 20 may have a somewhat different cross-sectional shape, and in that instance the carrier arms 30 as well as the passageway associated with each fixture arm 20 would have a similar, corresponding cross-sectional shape. For example, one of the fixture arms 20 may have a rectangular cross-sectional shape, another arm 20 may have a generally "T"-shaped configuration (such as shown in FIG. 4) while other fixture arms 20 may have a "X"-shaped configuration or an oval-shaped configuration in cross-sectional view. Such different cross-sectional shapes, when employed in connection with a single transfer tray 22, function as keys and mating keyways to help ensure that each passageway 40 receives the correct carrier arm 30. As a result, the practitioner is assured that the correct appliance 28 is ultimately bonded to the correct corresponding tooth 38.

Optionally, a computer may be used to assist in calculating the proper orientation of the appliances 28 on the respective teeth 38 as may be required to move the teeth 38 to desired positions. Such a method is especially useful when digital information has been created as described above defining the shape and location of the maloccluded teeth with respect to the patient's jaw. As an example, the methods described in U.S. Pat. No. 5,011,405 (which is expressly incorporated by reference herein) can be used to calculate the proper position of the appliances 28 on the teeth 38. Such a method can optionally include the steps of generating a mathematical model of the maloccluded teeth as positioned on the jaw from the digitized information, and calculating the finished position in the jaw to which the maloccluded teeth are to be moved from the digitized information. The digital information can be used if desired to make a custom appliance or to modify standard appliances to facilitate treatment. For example, brackets with certain patent-specific characteristics such as a certain torque and/or angulation can be made. Moreover, the digital information may be used to form an archwire for use with the appliances. The automated, robotic equipment described above may be used in carrying out such a method.

Figure 7:
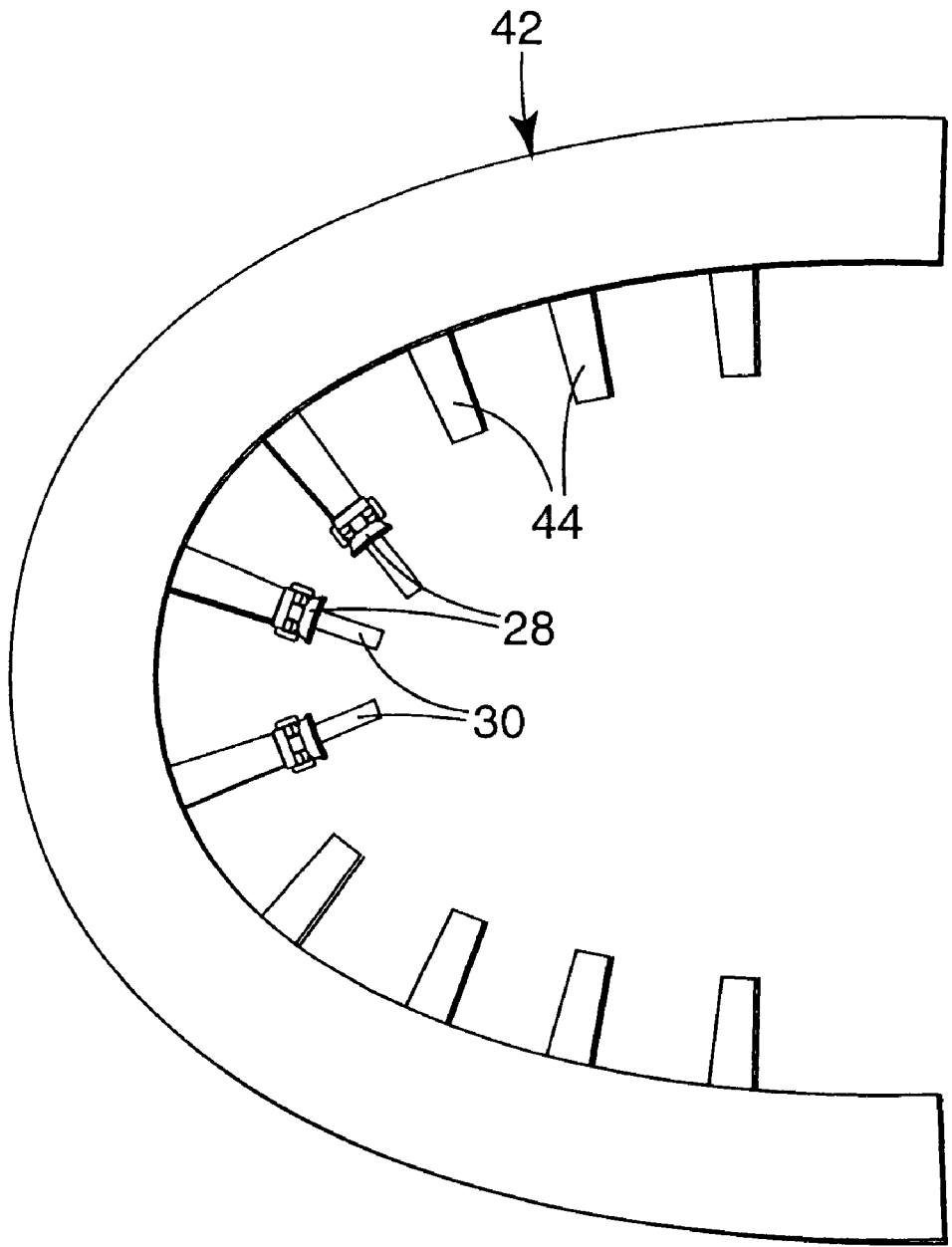
FIG. 7 is a schematic illustration depicting a master fixture for supporting fixture components or orthodontic appliances according to alternative embodiments of the invention.

As another alternative, the digital information defining the shape and the location of the maloccluded teeth with respect to the patient's jaw as described above may be utilized to make a transfer tray (such as the transfer tray 22) or tray section without making a physical replica dental arch 10. In accordance with this alternative embodiment, the digitized information can be used, for example, in association with stereolithographic apparatus to custom-make the transfer tray 22 with a channel complemental to the shape of the patient's dental arch as determined by digital data representative of the patient's arch or arch section or by a virtual replica arch or arch section created by a computer. A master fixture 42 as shown in FIG. 7 could be provided to support individual fixture components (such as fixture components 16) or appliances in a desired orientation as determined by a computer program while the transfer tray 22 is made. In that method, the use of appliance analogs (such as analogs 18) is optional, and alternatively the carrier arms 30 releasably supporting the appliances 28 can be embedded in the transfer tray 22 as the transfer tray 22 is made. Optionally, the master fixture 42 includes an array of movable robotic arms 44, each holding one of the appliances or appliance analogs at a certain orientation relative to the remaining appliances or appliance analogs in accordance with the digital data and according to software that determines optimal orientations for efficient orthodontic treatment.

As a further alternative, digital data defining the shape and the location of the maloccluded teeth with respect to the patient's jaw may be used to make a transfer tray (such as tray 22) or tray section without making a physical replica dental arch 10 and also without embedding either fixture arms (such as arms 20) or carrier arms (such as arms 30) in the matrix material as the tray or tray section is made. In this alternative, stereolithographic apparatus is used to custom-make the tray or tray section and to also make passageways (such as passageways 40). Optionally, the passageways are cut in the tray or tray section in a subsequent step using, for example, a machining process. Once the tray or tray section is made, the carrier arms are inserted into the passageways, either by hand or in an automated process.

Additionally, the transfer tray need not be fully match all of the patient's underlying tooth structure. For example, the tray may contact the tooth structure only at certain, spaced-apart regions. Such partial contact may be satisfactory so long as the regions are of sufficient size and configuration to ensure that the practitioner will be able to place the tray in its proper orientation in the oral cavity without undue effort.

The above methods in the various embodiments may be used in the level-arch technique as well as in other techniques as may be preferred by some practitioners. Optionally, the appliances and the archwires may be custom made using in part the digital information described above, or may be selected from a set of "standard" appliances and archwires. Optionally, an automated selection of optimal appliances and archwires is made from commercially available, off-the shelf products.

Once the adhesive has sufficiently hardened to bond the appliance 28 to the underlying tooth 38, the carrier arm 30 is moved in a buccolabial direction to disengage the appliance 28. During such movement, the stirrups 32 deflect outwardly and the slot segment (if present) disengages the archwire slot of the appliance 28 in order to allow the appliance 28 to detach from the carrier arm 30. Optionally, the carrier arms 30 can be withdrawn and detached from the transfer tray 22 before removal of the transfer tray 22 from the patient's oral cavity. As another alternative, the carrier arms 30 can remain connected to the transfer tray 22 while the latter is removed from the oral cavity.

The method set out above has been described in connection with orthodontic treatment of the patient's upper dental arch, but could also be used for treatment of the lower dental arch as well. Other variations and modifications of the embodiments described above may also be employed. Accordingly, the invention should not be deemed limited to the presently preferred embodiments that are described in detail above, but instead only by a fair scope of the claims that follow along with their equivalents.

What is claimed is:

1. A method of bonding an orthodontic appliance to a tooth comprising the steps of:

creating a replica of a patient's tooth structure;

releasably connecting at least one fixture component to the replica, wherein each fixture component includes an orthodontic appliance analog and an arm connected to the appliance analog, and wherein each appliance analog is positioned on the replica at a location corresponding to a location on the patient's tooth structure where an orthodontic appliance is to be received;

making a transfer tray by placing matrix material over at least a portion of the replica;

detaching the transfer tray from the replica;

replacing each appliance analog with an orthodontic appliance;

applying an orthodontic adhesive on at least one of the patient's tooth structure and each orthodontic appliance;

placing the transfer tray over the tooth structure; and moving each arm relative to the transfer tray in order to bring each orthodontic appliance into contact with the patient's tooth structure.

2. The method of claim 1 wherein the step of making a transfer tray includes the step of placing matrix material over at least a portion of at least one arm.

3. The method of claim 2, wherein each arm has a different cross-sectional configuration than the cross-sectional configuration of adjacent arms.

4. The method of claim 1 and including the step of providing each appliance analog with a base having an overall mesial-distal dimension that is larger than the mesial-distal overall dimension of the corresponding orthodontic appliance.

5. The method of claim 1, wherein the step of connecting at least one fixture component to the replica includes the step of providing a robotic arm to place each fixture component on the replica.

6. The method of claim 1, wherein the step of creating a replica of the patient's tooth structure is carried out by the use of digital data.

7. The method of claim 1, wherein the step of making the transfer tray includes the step of making portions that extend along mesial and distal sides of the appliance analog.

8. The method of claim 7, wherein the step of detaching the transfer tray from the replica includes the step of detaching each appliance analog from the replica.

9. The method of claim 1 and including the step of replacing the arm connected to the appliance analog with a carrier that is releasably connected to the appliance.

10. The method of claim 9, wherein the carrier is releasably coupled to the appliance by stirrups that matingly engage tiewings of the appliance.

11. A method of bonding an orthodontic appliance to a tooth comprising the steps of:

creating a replica of a patient's tooth structure;

releasably connecting at least one fixture component to the replica, wherein each fixture component is positioned on the replica at a location corresponding to a location on the patient's tooth structure where an orthodontic appliance is to be received;

making a transfer tray by placing matrix material over at least a portion of the replica as well as over at least a portion of at least one fixture component;

detaching the transfer tray from the replica;

disconnecting at least a portion of at least one fixture component from the transfer tray;

connecting at least one orthodontic appliance to the transfer tray at respective location(s) corresponding to the previous location(s) of at least one of the disconnected fixture components or component portions;

applying an orthodontic adhesive on at least one of the patient's tooth structure and each orthodontic appliance to be bonded; and placing the transfer tray with each orthodontic appliance over the patient's corresponding tooth structure in order to bond each orthodontic appliance to the tooth structure.

12. The method of claim 11, wherein each fixture component includes an appliance analog and a fixture arm extending from the appliance analog, and wherein the step of making a transfer tray includes the step of placing the matrix material over at least a portion of at least one fixture arm.

13. The method of claim 12, wherein the step of connecting at least one orthodontic appliance to the transfer tray includes the step of providing a carrier arm that is releasably secured to the appliance and is connected to the transfer tray.

14. The method of claim 13, and including the step of sliding each carrier arm relative to the transfer tray after the transfer tray is placed over the tooth structure in order to bring the corresponding appliance into contact with the tooth structure.

15. The method of claim 13, wherein each carrier arm includes at least one flexible stirrup for coupling to a tiewing of the appliance.

16. The method of claim 12, and including the step of providing each appliance analog with a base that is larger than the base of the corresponding appliance in a mesial-distal direction.

17. The method of claim 11, wherein the step of detaching the transfer tray from the replica includes the step of detaching each fixture component from the replica.

18. The method of claim 11, wherein the step of releasably connecting at least one fixture component to the replica includes the step of providing a robotic arm to place each fixture component on the replica.

19. The method of claim 11, wherein the step of creating a replica of a patent's tooth structure is carried out by the use of digital data.

20. The method of claim 19 and including the step of at least partially making the orthodontic appliance using in part the digital data.

21. The method of claim 20 and further including the step of at least partially making an archwire using in part the digital data.

22. A method of bonding an orthodontic appliance to a tooth comprising the steps of:
   making a transfer tray that corresponds to a negative image of at least part of the patient's tooth structure;
   connecting at least one carrier arm to the transfer tray in such a manner that at least one carrier arm is movable relative to the tray;
   releasably coupling an orthodontic appliance to at least one carrier arm;
   placing the tray over the patient's tooth structure;
   applying an orthodontic adhesive on at least one of the patient's tooth structure and each appliance;
   moving at least one carrier arm relative to the tray in order to bond the appliance coupled to such arm(s) to the patient's tooth structure; and
   sliding a tool along sides of the appliances in order to remove any excess adhesive,
   wherein the step of making a transfer tray includes the step of making portions that extend along mesial and distal sides of at least one appliance at a position spaced from the appliance in order to facilitate removal of any excess adhesive.

23. The method of claim 22, wherein the step of making a transfer tray is carried out by the use of digital data.

24. The method of claim 23 and including the step of at least partially making the orthodontic appliance using in part the digital data.

25. The method of claim 22, and further including the step of at least partially making an archwire using in part the digital data.

26. The method of claim 22, wherein the step of making a transfer tray includes the steps of creating a replica of a patient's tooth structure and placing matrix material over at least a portion of the replica.

27. The method of claim 22, wherein the step of releasably coupling an orthodontic appliance to each carrier arm includes the step of providing stirrups that releasably couple to tiewings of the appliance.

28. The method of claim 22, wherein the step of releasably coupling an orthodontic appliance to each carrier arm further includes the step of providing each carrier arm with a slot segment for reception into an archwire slot of the appliance.

29. The method of claim 22, wherein the step of moving the carrier arm relative to the tray includes the step of sliding such carrier arm(s) in a passageway of the tray.

30. The method of claim 22, wherein the step of making portions that extend along mesial and distal sides of at least one appliance includes the step of making portions that extend occlusally of the appliance.

31. A method of bonding an orthodontic appliance to a tooth comprising the steps of:
   making a transfer tray that corresponds to a negative image of at least part of the patient's tooth structure;
   connecting at least one carrier arm to the transfer tray in such a manner that at least one carrier arm is movable relative to the tray;
   releasably coupling an orthodontic appliance to at least one carrier arm;
   placing the tray over the patient's tooth structure;
   applying an orthodontic adhesive on at least one of the patient's tooth structure and each appliance;
   moving at least one carrier arm relative to the tray in order to bond the appliance coupled to such arm(s) to the patient's tooth structure,
   wherein the step of making a transfer tray includes the step of making portions that extend along mesial and distal sides of at least one appliance at a position spaced from the appliance in order to facilitate removal of any excess adhesive,
   wherein the step of making a transfer tray also includes the steps of creating a replica of a patient's tooth structure and placing matrix material over at least a portion of the replica;
   releasably connecting at least one fixture component to the replica, wherein each fixture component includes an orthodontic appliance analog; and
   replacing each appliance analog with an orthodontic appliance.

32. An orthodontic transfer tray assembly comprising:
   at least one orthodontic appliance;
   at least one carrier arm, wherein at least one carrier arm is connected to a corresponding orthodontic appliance; and
   a transfer tray including an occlusal section for extending over occlusal portions of a patient's tooth structure and a buccolabial section for extending over buccolabial portions of a patient's tooth structure, wherein each carrier arm is coupled to the tray, wherein the buccolabial section includes a generally "U"-shaped recess for receiving each appliance, and wherein each recess extends along the mesial, occlusal and distal sides of the corresponding appliance in spaced relationship to the appliance when the appliance is in contact with the patient's tooth structure, and wherein each recess is open to enable access to the mesial, occlusal and distal sides of the corresponding appliance.

33. The orthodontic transfer tray assembly of claim 32 wherein each carrier arm is movably coupled to the tray.

34. The orthodontic transfer tray assembly of claim 33 wherein each carrier arm is coupled to the occlusal section of the tray.

35. The orthodontic transfer tray assembly of claim 33 wherein the transfer tray includes at least one passageway for slidably receiving a corresponding carrier arm.

36. The orthodontic transfer tray assembly of claim 32 wherein each carrier arm is releasably connected to each corresponding appliance by stirrups that engage tiewings of the appliance.

37. An orthodontic transfer tray assembly of claim 32 wherein each carrier arm includes a slot segment that is received in an archwire slot of the appliance.

38. An orthodontic transfer tray assembly of claim 32 wherein the transfer tray includes portions that extend occlusally of each appliance.

39. An orthodontic transfer tray assembly comprising:
at least one orthodontic appliance,
at least one carrier arm, wherein at least one carrier arm is connected to a corresponding orthodontic appliance; and
a transfer tray including an occlusal section for extending over occlusal portions of a patient's tooth structure and a buccolabial section for extending over buccolabial portions of a patient's tooth structure, wherein each carrier arm is coupled to the tray, wherein the buccolabial section includes a generally "U"-shaped recess for receiving each appliance, and wherein each recess extends along the mesial, occlusal and distal sides of the corresponding appliance in spaced relationship to the appliance when the appliance is in contact with the patient's tooth structure,
wherein each carrier arm is movably coupled to the tray, and wherein each carrier arm extends completely through the occlusal section.

40. An orthodontic transfer tray assembly comprising:
at least one orthodontic appliance;
at least one carrier arm, wherein each carrier arm is connected to a corresponding orthodontic appliance; and
a transfer tray including a generally "U"-shaped channel for extending along the patient's dental arch, the tray including a lingual section, a buccolabial section and an occlusal section interconnecting the lingual section and the buccolabial section, wherein the lingual section and the buccolabial section are resilient and have sufficient depth in an occlusal-gingival direction to present undercut regions that snap-fit over corresponding tooth structure for self-retaining the tray in engagement with the tooth structure in releasable fashion, and wherein the tray includes at least one passageway extending in the occlusal section for receiving a respective carrier arm.

41. An orthodontic transfer tray assembly according to claim 40 wherein the buccolabial section includes a generally U-shaped recess surrounding each appliance, and wherein each recess presents a space between the tray and mesial, occlusal and distal sides of the corresponding appliance.

42. An orthodontic transfer tray assembly according to claim 40 wherein each carrier arm is movably coupled to the tray.

43. An orthodontic transfer tray assembly according to claim 42 wherein each carrier arm is slidingly received in a corresponding passageway.

44. An orthodontic transfer tray assembly according to claim 40 wherein each carrier arm is releasably connected to each corresponding appliance by stirrups that engage tiewings of the appliance.

45. An orthodontic transfer tray assembly according to claim 40 wherein the transfer tray includes portions that extend occlusally of each appliance.

46. A method of making a transfer tray assembly for an orthodontic patient comprising the steps of:
supporting at least two orthodontic appliances or appliance analogs at selected, spaced-apart positions;
coupling a corresponding arm to each orthodontic appliance or appliance analog;
placing a quantity of matrix material over at least a portion of each arm in order to connect the arms together, and wherein at least a portion of the matrix material has a configuration matching at least a portion of the orthodontic patient's dental arches;
allowing the matrix material to harden to form a tray; and
sliding each arm relative to the tray after the matrix material has hardened.

47. The method of according to claim 46 wherein each arm has a different cross-sectional configuration than the cross-sectional configuration of adjacent arms.

48. The method of claim 46 wherein a portion of the matrix material extends along mesial and distal sides of each orthodontic appliance or appliance analog.

49. The method of claim 46 wherein each arm is slidable relative to the tray.

50. The method of claim 46 wherein the step of making a transfer tray is carried out by use of digital data.

51. A method of making a transfer tray for an orthodontic patient comprising the steps of:
creating a replica of the patient's tooth structure;
releasably connecting at least one fixture component to the replica, wherein each fixture component includes an orthodontic appliance analog and an arm connected to the appliance analog, and wherein each appliance analog is positioned on the replica at a location corresponding to a location on the patient's tooth structure where an orthodontic appliance is to be received;
placing matrix material over at least a portion of the replica as well as over at least a portion of the arm of at least one fixture component;
detaching the transfer tray from the replica; and
replacing each appliance analog with an orthodontic appliance.

52. The method of claim 51 wherein each arm has a different cross-sectional configuration than the cross-sectional configuration of adjacent arms.

53. The method of claim 51 and including the step of providing each appliance analog with a base having an overall mesial-distal dimension that is larger than the mesial-distal overall dimension of the corresponding orthodontic appliance.

54. The method of claim 51, wherein the step of connecting at least one fixture component to the replica includes the step of providing a robotic arm to place each fixture component on the replica.

55. The method of claim 51, wherein the step of creating a replica of the patient's tooth structure is carried out by the use of digital data.

56. The method of claim 55, and including the step of at least partially making the orthodontic appliance using in part the digital data.

57. The method of claim 55, and including the step of at least partially making an archwire using in part the digital data.

58. The method of claim 51, wherein the step of making the transfer tray includes the step of making portions that extend along mesial and distal sides of the appliance analog.

59. The method of claim 51, wherein the step of detaching the transfer tray from the replica includes the step of detaching each appliance analog from the replica.

60. The method of claim 51 and including the step of replacing the arm connected to the appliance analog with a carrier that is releasably connected to the appliance.

61. The method of claim 51, wherein the carrier is releasably coupled to the appliance by stirrups that matingly engage tiewings of the appliance.

* * * * *

UNITED STATES PATENT AND TRADEMARK OFFICE
CERTIFICATE OF CORRECTION

PATENT NO.   : 6,123,544
DATED        : September 26, 2000
INVENTOR(S)  : Cleary, James D.

Page 1 of 1

It is certified that error appears in the above-identified patent and that said Letters Patent is hereby corrected as shown below:

Column 3,
Line 64, insert -- in -- following "group" and preceding "a".

Column 9,
Line 16, delete "An" and insert in place thereof -- As --.

Column 12,
Line 67, delete "caries" and insert in place thereof -- cavities --.

Column 13,
Line 61, delete "arm" and insert in place thereof -- arms --.
Line 64, "releasably" and insert in place thereof -- releasable --.
Lines 66-67, delete "connected" and insert in place thereof -- connect --.

Column 15,
Line 13, delete "be".

Column 17,
Line 23, delete "patent's" and insert in place thereof -- patient's --

Signed and Sealed this

Fourteenth Day of May, 2002

*Attest:*

*Attesting Officer*

JAMES E. ROGAN
*Director of the United States Patent and Trademark Office*